United States Patent
Calvosa et al.

(10) Patent No.: US 9,339,303 B2
(45) Date of Patent: May 17, 2016

(54) MODULAR VERTEBRAL STABILIZER

(71) Applicant: Lanx, S.R.L., Medolla (IT)

(72) Inventors: Giuseppe Calvosa, Pisa (IT); Patrizio Cervellini, Vicenza (IT); Miria Tenucci, Lucca (IT)

(73) Assignee: LANX, S.R.L., Medolla (IT)

( * ) Notice: Subject to any disclaimer, the term of this patent is extended or adjusted under 35 U.S.C. 154(b) by 0 days.

(21) Appl. No.: 14/467,437

(22) Filed: Aug. 25, 2014

(65) Prior Publication Data

US 2014/0364914 A1 Dec. 11, 2014

Related U.S. Application Data

(63) Continuation of application No. 13/132,744, filed as application No. PCT/EP2009/067208 on Dec. 15, 2009, now abandoned.

(30) Foreign Application Priority Data

Dec. 17, 2008 (IT) .............................. MI2008A2238

(51) Int. Cl.
*A61B 17/70* (2006.01)
(52) U.S. Cl.
CPC ............ *A61B 17/7035* (2013.01); *A61B 17/701* (2013.01); *A61B 17/7007* (2013.01); *A61B 17/7031* (2013.01); *A61B 17/7053* (2013.01)
(58) Field of Classification Search
CPC ........................ A61B 17/7038; A61B 17/7043
USPC .................................................. 606/246–278
See application file for complete search history.

(56) References Cited

U.S. PATENT DOCUMENTS

| | | | | | |
|---|---|---|---|---|---|
| 3,997,138 | A | * | 12/1976 | Crock | A61B 17/7001 248/67.5 |
| 4,112,935 | A | * | 9/1978 | Latypov | A61B 17/7052 606/263 |
| 4,604,995 | A | * | 8/1986 | Stephens | A61B 17/7053 606/261 |

(Continued)

FOREIGN PATENT DOCUMENTS

| WO | WO-2007060534 A2 | 5/2007 |
|---|---|---|
| WO | WO2010069967 A1 | 6/2010 |
| WO | WO-2010069967 A1 | 6/2010 |

OTHER PUBLICATIONS

International Search Report and Written Opinion from counterpart application PCT/EP2009/067208 (Jun. 2011).

(Continued)

*Primary Examiner* — Ellen C Hammond
*Assistant Examiner* — Stuart S Bray
(74) *Attorney, Agent, or Firm* — Schwegman Lundberg & Woessner, P.A.

(57) ABSTRACT

A stabilizer device for the spinal column, comprising first engagement means and second engagement means, which are adapted to be connected to each other by a rod-like element, the first and second engagement means being adapted to be fitted on first and second pedicle screws, which are adapted to be in turn inserted in two adjacent vertebrae, the first and second engagement means being fixable on the pedicle screws; the first and second engagement means accommodate bearing means, which are adapted to rotate within the first and second engagement means and to be fitted on the pedicle screws, in order to allow the fitting of the first and second engagement means on the pedicle screws.

15 Claims, 3 Drawing Sheets

(56) References Cited

U.S. PATENT DOCUMENTS

| | | | |
|---|---|---|---|
| 4,790,303 A * | 12/1988 | Steffee | A61B 17/7022 606/263 |
| 5,180,393 A * | 1/1993 | Commarmond | A61B 17/7007 606/254 |
| 5,387,212 A * | 2/1995 | Yuan | A61B 17/701 606/264 |
| 5,417,690 A * | 5/1995 | Sennett | A61B 17/82 606/263 |
| 5,672,175 A * | 9/1997 | Martin | A61B 17/025 606/105 |
| 5,725,582 A * | 3/1998 | Bevan | A61B 17/7022 24/129 W |
| 6,086,590 A * | 7/2000 | Margulies | A61B 17/7053 606/263 |
| 6,312,431 B1 * | 11/2001 | Asfora | A61B 17/7068 606/263 |
| 6,488,683 B2 * | 12/2002 | Lieberman | A61B 17/70 606/263 |
| 6,514,255 B1 * | 2/2003 | Ferree | A61B 17/7053 606/103 |
| 6,551,320 B2 * | 4/2003 | Lieberman | A61B 17/7022 606/263 |
| 6,626,944 B1 * | 9/2003 | Taylor | A61B 17/7062 606/249 |
| 7,458,981 B2 * | 12/2008 | Fielding | A61B 17/7062 606/279 |
| 7,481,828 B2 * | 1/2009 | Mazda | A61B 17/7053 606/263 |
| 7,520,887 B2 * | 4/2009 | Maxy | A61B 17/7062 606/248 |
| 7,588,575 B2 * | 9/2009 | Colleran | A61B 5/103 606/252 |
| 7,621,912 B2 * | 11/2009 | Harms | A61B 17/645 606/246 |
| 7,785,352 B2 * | 8/2010 | Snyder | A61B 17/7001 606/263 |
| 7,799,060 B2 * | 9/2010 | Lange | A61B 17/7022 606/257 |
| 7,947,064 B2 * | 5/2011 | Bergeron | A61B 17/1655 606/103 |
| 8,029,541 B2 * | 10/2011 | Alamin | A61B 17/7062 606/248 |
| 8,029,544 B2 * | 10/2011 | Hestad | A61B 17/7031 606/254 |
| 8,057,472 B2 | 11/2011 | Walker et al. | |
| 8,105,363 B2 | 1/2012 | Fielding et al. | |
| 8,114,135 B2 * | 2/2012 | Malandain | A61B 17/7055 606/151 |
| 8,162,993 B2 * | 4/2012 | Ferree | A61B 17/0401 606/228 |
| 8,177,810 B2 | 5/2012 | Ferree | |
| 8,182,513 B2 * | 5/2012 | Calvosa | A61B 17/701 606/246 |
| 8,216,275 B2 | 7/2012 | Fielding et al. | |
| 8,337,528 B2 * | 12/2012 | Ferree | A61B 17/7022 606/263 |
| 8,337,529 B2 * | 12/2012 | Ferree | A61B 17/06166 606/263 |
| 8,357,181 B2 * | 1/2013 | Lange | A61B 17/7065 606/248 |
| 8,394,124 B2 * | 3/2013 | Biyani | A61B 17/7022 606/246 |
| 8,403,961 B2 * | 3/2013 | Fielding | A61B 17/7053 606/246 |
| 8,454,660 B2 | 6/2013 | Alamin et al. | |
| 8,454,662 B2 * | 6/2013 | Bethell | A61B 17/70 606/263 |
| 8,470,002 B2 * | 6/2013 | Allard | A61B 17/7011 606/258 |
| 8,486,110 B2 | 7/2013 | Fielding et al. | |
| 8,562,653 B2 * | 10/2013 | Alamin | A61B 17/7062 606/263 |
| 8,617,214 B2 * | 12/2013 | Malek | A61B 17/7022 606/257 |
| 8,632,572 B2 * | 1/2014 | Darst Rice | A61B 17/8869 606/263 |
| 8,641,734 B2 * | 2/2014 | Moumene | A61B 17/7028 606/246 |
| 2002/0107524 A1 * | 8/2002 | Magana | A61B 17/7059 606/103 |
| 2004/0260287 A1 * | 12/2004 | Ferree | A61B 17/7005 606/252 |
| 2005/0143737 A1 * | 6/2005 | Pafford | A61B 17/701 606/257 |
| 2005/0154390 A1 * | 7/2005 | Biedermann | A61B 17/7035 128/898 |
| 2005/0267470 A1 * | 12/2005 | McBride | A61B 17/7022 606/263 |
| 2006/0084983 A1 * | 4/2006 | Kim | A61B 17/7065 606/914 |
| 2006/0195090 A1 * | 8/2006 | Suddaby | A61B 17/7011 606/263 |
| 2006/0276896 A1 * | 12/2006 | Fallin | A61B 17/82 623/16.11 |
| 2007/0043356 A1 * | 2/2007 | Timm | A61B 17/7007 606/279 |
| 2008/0065114 A1 | 3/2008 | Stone et al. | |
| 2008/0161853 A1 | 7/2008 | Arnold et al. | |
| 2008/0177306 A1 * | 7/2008 | Lamborne | A61B 17/7065 606/246 |
| 2008/0262549 A1 * | 10/2008 | Bennett | A61B 17/7062 606/263 |
| 2009/0024165 A1 * | 1/2009 | Ferree | A61B 17/7022 606/246 |
| 2009/0088799 A1 * | 4/2009 | Yeh | A61B 17/7005 606/246 |
| 2009/0099608 A1 * | 4/2009 | Szczesny | A61B 17/7028 606/257 |
| 2009/0112207 A1 * | 4/2009 | Walker | A61B 17/7016 606/57 |
| 2009/0163954 A1 * | 6/2009 | Kwak | A61B 17/7007 606/257 |
| 2009/0198282 A1 | 8/2009 | Fielding et al. | |
| 2010/0042154 A1 * | 2/2010 | Biedermann | A61B 17/7004 606/254 |
| 2010/0106194 A1 * | 4/2010 | Bonutti | A61B 17/0218 606/279 |
| 2011/0288589 A1 * | 11/2011 | Fielding | A61B 17/7053 606/263 |
| 2012/0123482 A1 | 5/2012 | Fielding et al. | |
| 2012/0130432 A1 * | 5/2012 | Ferree | A61B 17/7014 606/279 |
| 2012/0136394 A1 | 5/2012 | Calvosa et al. | |
| 2012/0209330 A1 | 8/2012 | Jahng et al. | |
| 2012/0221054 A1 * | 8/2012 | Jackson | A61B 17/7001 606/254 |
| 2012/0289962 A1 | 11/2012 | Hulliger et al. | |
| 2013/0013005 A1 | 1/2013 | Ferree | |
| 2013/0096632 A1 | 4/2013 | Chico Roca | |
| 2013/0123841 A1 | 5/2013 | Lyon | |
| 2013/0158609 A1 | 6/2013 | Mikhail et al. | |
| 2013/0160276 A1 | 6/2013 | Chico Roca | |
| 2013/0282063 A1 | 10/2013 | Bhatnagar et al. | |

OTHER PUBLICATIONS

"U.S. Appl. No. 13/132,744, Non Final Office Action mailed Feb. 25, 2014", 15 pgs.

* cited by examiner

MODULAR VERTEBRAL STABILIZER

CROSS-REFERENCE TO RELATED APPLICATIONS

This application is a continuation of U.S. patent application Ser. No. 13/132,744 filed on Jan. 30, 2012, which is a U.S. National Phase of PCT/EP2009/067208 filed Dec. 15, 2009 which claims priority to Italian Application Serial Number MI2008A002238 filed Dec. 17, 2008. The entire disclosures of each of the above applications are incorporated herein by reference.

FIELD

The present invention relates to a modular vertebral stabilizer. More particularly, it relates to a modular vertebral stabilizer that is adapted to connect at least two adjacent vertebrae to each other by using at least two connecting elements which allow some certain limited movement to the vertebrae.

BACKGROUND

As is known, many pathologies related to the functionality of the spinal column are treated by total or partial immobilization, particularly with a technique known as "intervertebral arthrodesis", with the aid of connection means and/or with the addition of portions of bone tissue which join such adjacent vertebrae.

Vertebral stabilization devices of the static and dynamic types are known in the art and have a screw that is adapted to be connected to a vertebra, and rigid elements or elements that have a limited mobility and have two ends which are jointly connected to the two screws connected to two adjacent vertebrae.

In particular, a dynamic stabilizing device, i.e., capable of allowing relative movement between the vertebrae, is disclosed in EP 0 669 109. This vertebral stabilizer comprises a spacing body, which is resistant to compression and is adapted to transfer forces between two screws implanted in the respective vertebrae, and a tensioning cord which is connected between the two screws described above and passes in an internal longitudinal cavity obtained in the spacing body.

However, this stabilizer has a drawback, due to the fact that it is directly assembled locally on the spinal column after inserting the screws in the vertebrae, with open surgery in a space that is close to the vertebra. Therefore, the surgical procedure that makes it possible to use such stabilization structure is highly invasive, since it is necessary to create enough space close to the vertebra to perform the various steps of assembly, with considerable difficulty for the surgeon, who has to arrange and assemble each individual element directly on the vertebra.

Moreover, the stabilizer described above does not allow a transverse connection between screws mounted on different vertebrae to transmit forces in a diagonal direction with respect to the axis of the spinal column.

Further, the tensioning cord must be threaded in the spacing body, and this requires a higher skill effort for the surgeon.

Moreover, the surgeon may need a stabilizer that has both static and dynamic portions, i.e., he may have to create a hybrid stabilizer, in which the portions can be chosen by the surgeon according to the characteristics of the pathology.

Known types of stabilizers do not allow creation of a stabilizer of the hybrid type that is totally modular, i.e., capable of adapting to all the configurations that the pathology of the patient may require and are decided on by the surgeon, for example rigid-dynamic-rigid, or dynamic-rigid-dynamic. WO2007/060534, in the name of this same Applicant as the present invention, discloses a vertebral stabilizer of the dynamic modular type, which is adapted to be assembled separately from the spinal column and then fitted onto the spinal column in a few seconds.

However, the known type of stabilizer device is unable to adapt to angle variations with which the pedicle screws might be fitted within the vertebrae, and therefore, if the positioning of such pedicle screws is not performed, in two adjacent vertebrae, with the same angle, the surgeon encounters difficulties in mounting the stabilizer device fitted over the heads of the pedicle screws.

SUMMARY

The aim of the present invention is to provide a device for stabilizing the spinal column which allows transverse connection between adjacent vertebrae, allowing different angles between pedicle screws inserted in adjacent vertebrae.

Within this aim, an object of the present invention is to provide a stabilizer device that can be assembled separately from the spinal column and then fitted onto said spinal column with reduced invasiveness for the patient.

Another object of the present invention is to provide a spinal column stabilizer device that is modular, allowing therefore provision of a hybrid stabilizer device, i.e., a device that is static at one end and dynamic at the opposite end.

Another object of the present invention is to provide a stabilizer device that is highly reliable, relatively simple to provide and at competitive costs.

This aim and these and other objects that will become better apparent hereinafter are achieved by a stabilizer device for the spinal column, comprising a first disk-like body and a second disk-like body, which are adapted to be connected to each other by a rod-like element, said first and second disk-like bodies being adapted to be fitted on first and second pedicle screws, which are adapted to be in turn inserted in two adjacent vertebrae, said first and second disk-like bodies being fixable on said pedicle screws, characterized in that said first and second disk-like bodies accommodate bearing means, which are adapted to rotate within said first and second disk-like bodies and to be fitted on said pedicle screws, in order to allow the fitting of said first and second disk-like bodies on said pedicle screws.

Further areas of applicability will become apparent from the description provided herein. The description and specific examples in this summary are intended for purposes of illustration only and are not intended to limit the scope of the present disclosure.

DRAWINGS

Further characteristics and advantages of the invention will become better apparent from the following detailed description of some preferred but not exclusive embodiments of the device according to the present invention, illustrated by way of non-limiting example in the accompanying drawings, wherein.

DETAILED DESCRIPTION

Figure 1:
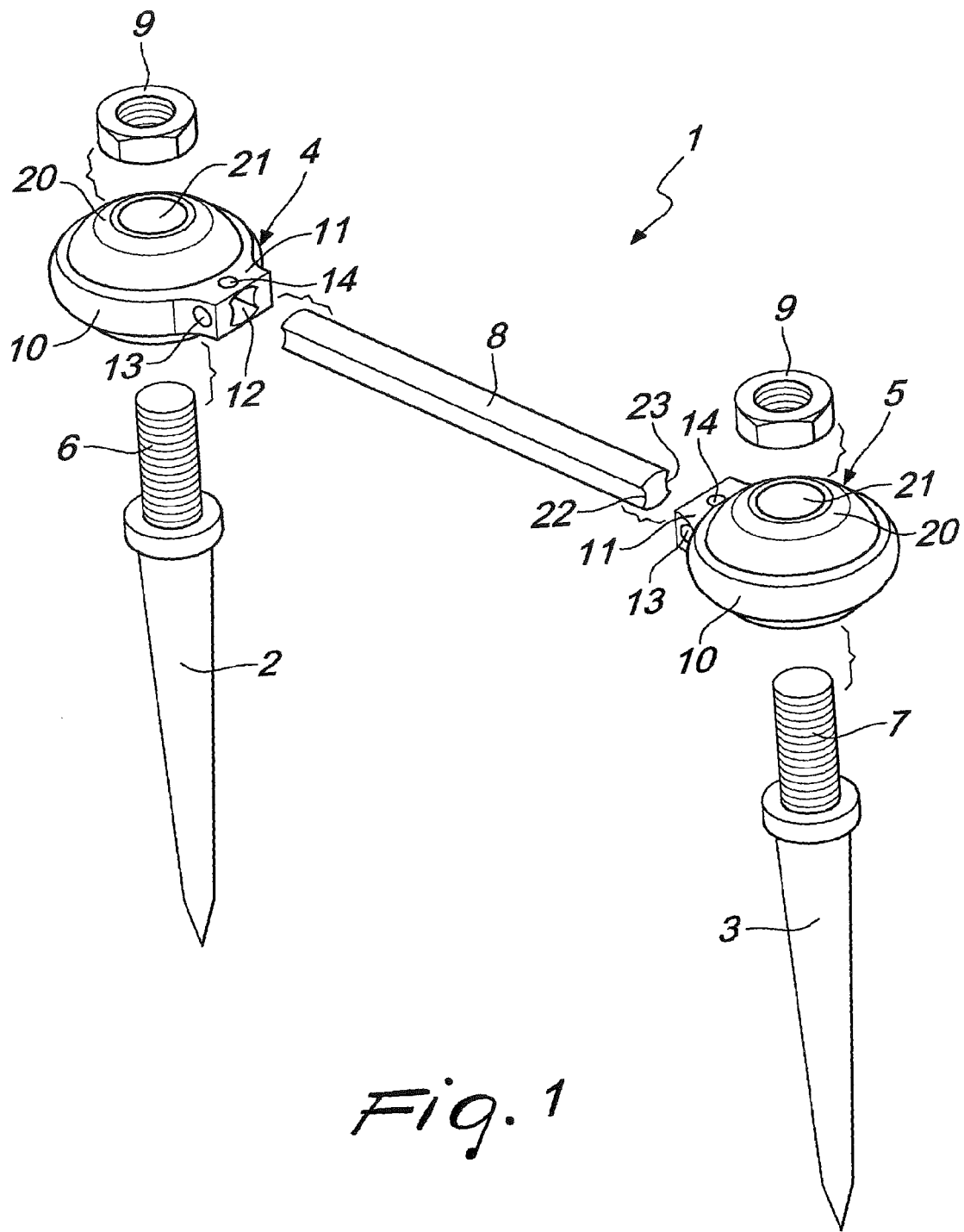
FIG. 1 is an exploded perspective view of a stabilizer device according to the present invention.

With reference to the figures, a stabilizer device according to the present invention, generally designated by the reference numeral 1, comprises first and second means for engaging a first pedicle screw 2 and a second pedicle screw 3, which are adapted to be inserted in two adjacent vertebrae to be connected to each other for mutual stabilization.

The pedicle screws are conveniently headless and cannulated, so that they can be screwed into the vertebrae.

First engagement means, designated by the reference numeral 4, and second engagement means, designated by the reference numeral 5, are adapted to be fitted from above on a threaded portion 6 and 7 respectively on the first pedicle screw 2 and on the second pedicle screw 3.

The first and second engagement means 4 and 5 are connected to each other by a rod-like element 8, of the bar type, which can be made of a rigid material, such as for example titanium, or of softer material, such as for example polyurethane, so as to give flexibility to the rod-like element.

Conveniently, there are locking means 9, constituted for example by nuts, for locking engagement means 4 and 5 on the threaded portions 6 and 7 of the first and second pedicle screws described earlier.

Conveniently, the engagement means 4 and 5 comprise a substantially circular body 10, which is provided with at least one protruding portion 11, which is adapted to form a seat 12 for the engagement of the rod-like element 8. The seat 12 formed in the protruding portion 11 is conveniently shaped so as to be complementary with respect to the shape of the rod-like element 8.

Conveniently, the protruding portion 11 of the circular body 10 is provided with at least one hole 13, which allows either the insertion of a fastening cord, as defined hereinafter, or of a locking grub, as also described hereinafter.

Conveniently, the protruding portion 11 can be provided with a second hole arranged on its upper face, i.e., the face designed to be arranged parallel to the spinal column, and is adapted to accommodate a fixing grub, which can allow further fixing of the cord described hereinafter.

Figure 2:
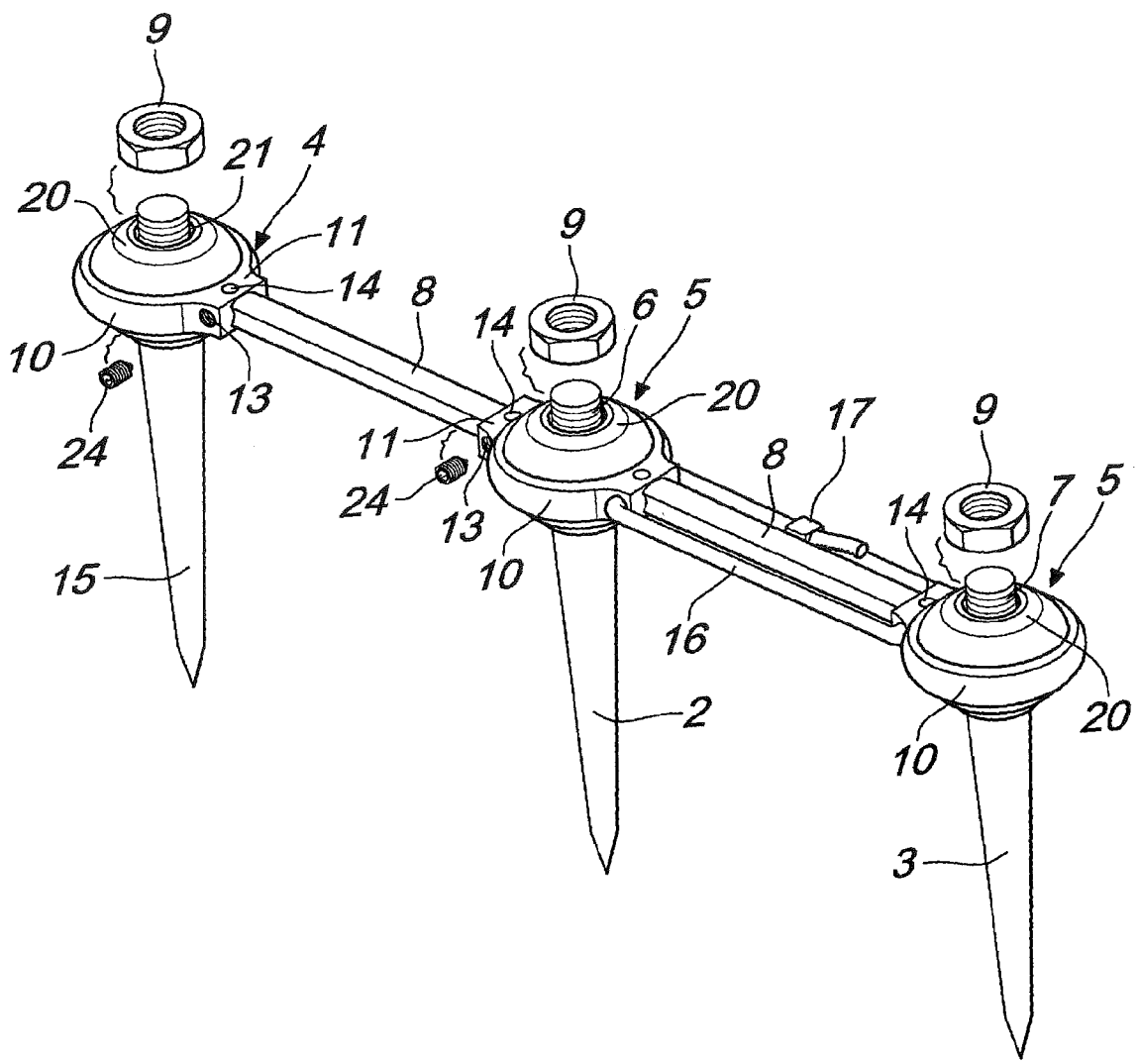
FIG. 2 is a perspective view of a second embodiment of the stabilizer device according to the present invention.
Figure 3:
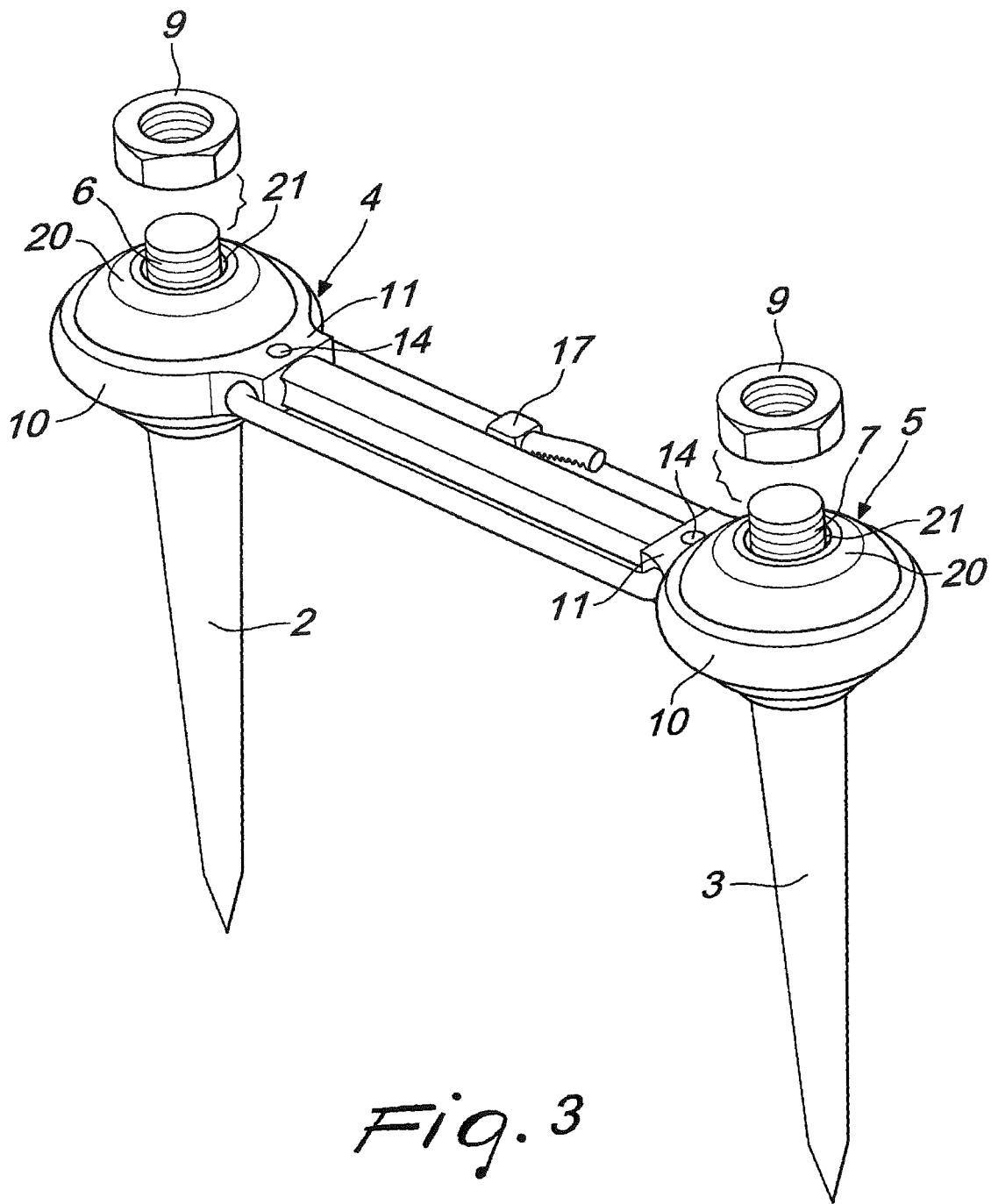
FIG. 3 is a perspective view of the stabilizer device of FIG. 1 in the assembled condition.

The circular or disk-like element 10 can be provided with a pair of protruding portions 11, which are diametrically opposite, as shown in FIG. 2, so as to create an element that is adapted to allow the connection of two rod-like elements, on either side, so as to mutually mate three pedicle screws inserted in three adjacent vertebrae.

In FIG. 2, the third pedicle screw, in addition to the first and second pedicle screws 2 and 3, is designated by the reference numeral 15. Such pedicle screws, despite having different reference numerals that designate them, are mutually identical.

In FIG. 2 there is also shown the presence of the cord cited above, designated by the reference numeral 16 and made for example of methyl methacrylate, which enters the holes 13 of the circular or disk-like elements 10 and lies in a closed circuit around the rod-like element 8, which in this case is made of elastic material.

Conveniently, the two ends of the cord 16, adapted to be mutually coupled so as to provide a cord that is closed in a loop around the rod-like element 8, are provided with respective tensioning means 17, which are adapted to allow tensioning of the cord 16.

Conveniently, the tensioning means 17 can be provided for example with one end of the cord which is provided with a set of teeth and the opposite end which is provided with a receptacle, like a hose clamp.

In this manner, the surgeon can perform, separately from the spinal column, a fastening of the cord 16 around the rod-like element 8 and then, once the stabilizer device has been assembled, said device can be fitted on the pedicle screws that are already accommodated in the holes provided in the vertebrae to be coupled in a stabilized manner.

Conveniently, the circular or disk-like body 10 is provided internally with a circular opening which accommodates bearing means 20, which are adapted to rotate within the circular or disk-like body 10, so as to allow the arrangement of the engagement means 4 at different angles between one screw and the screw that is adjacent to it, thus also allowing a slight positioning error of the pedicle screws inserted in the vertebrae that are to be mutually coupled.

Conveniently, the bearing 20 is provided with a central hole 21, which is adapted to allow the insertion of the threaded portion 6 of the pedicle screw 2 or of the threaded portion 7 of the pedicle screw 3.

Conveniently, the rod-like element 8 has a circular cross-section with a pair of lateral recesses 22 and 23 which are adapted to accommodate the cord 16 when it is fastened around the rod-like element 8. FIG. 2 shows threaded grubs 24, which are inserted in the protruding portions 11 of the disk-like bodies 10 so as to fasten the rod-like element 8.

FIG. 2 is a view of the provision of a hybrid stabilizer device, i.e., a partly dynamic and partly static stabilizer device, which is obtained by coupling three pedicle screws to each other with a first rod-like element 8 of the rigid type and a second rod-like element 8 of the elastic type, with which the cord 16 fastened around the rod-like element 8 is associated.

The bearing element 20 accommodated within the hole formed in the disk-like body 10 is adapted to rotate within said hole, so as to behave like a sort of ball that can rotate in all directions within the hole of the disk-like body 10.

In practice it has been found that the stabilizer device according to the present invention fully achieves the intended aim and objects, since it allows to be assembled away from the spinal column, allows to adapt to different implantation angles of the pedicle screws within the vertebrae, and allows to provide hybrid structures with rigid portions and elastic portions.

Moreover, this modular system allows to change, whenever necessary, only the disk-like bodies and the bar with a different bar or rod, leaving the screws inserted in the pedicles, with great advantage for the patient and for the surgeon.

The stabilizer device thus conceived is susceptible of numerous modifications and variations, all of which are within the scope of the appended claims; all the details may further be replaced with other technically equivalent elements.

In practice, the materials used, as well as the contingent shapes and dimensions, may be any according to requirements and to the state of the art.

The disclosures in Italian Patent Application No. MI2008A002238 from which this application claims priority are incorporated herein by reference.

Where technical features mentioned in any claim are followed by reference signs, those reference signs have been included for the sole purpose of increasing the intelligibility of the claims and accordingly, such reference signs do not have any limiting effect on the interpretation of each element identified by way of example by such reference signs.

What is claimed is:
1. A stabilizer apparatus for a spinal column, comprising:
a first engagement member housing a bearing and having at least one protruding portion with a seat sized to receive a rod-like element, where the protruding portion includes a through hole having a longitudinal axis extending transverse with a longitudinal axis of the rod- like element, and the bearing is configured to receive a first pedicle screw and rotate within the first engagement member;

a second engagement member housing a bearing and having at least one protruding portion with a seat sized to receive a rod-like element, where the protruding portion includes a through hole having a longitudinal axis extending transverse with a longitudinal axis of the rod-like element, and the bearing is configured to receive a second pedicle screw and rotate within the second engagement member, wherein the first engagement member is connected via the rod-like element to the second engagement member and a cord extends through the through holes of the protruding portions of the first and second engagement members with its ends coupled together to form a closed loop around the rod-like element, the protruding portions of the first and second engagement members facing each other.

2. The stabilizer apparatus of claim 1 wherein at least one of the first engagement member and the second engagement member includes a second protruding portion arranged diametrically opposite the first protruding portion and with a seat sized to receive another rod-like element.

3. The stabilizer apparatus of claim 1 wherein the rod-like element is comprised of elastic material.

4. The stabilizer apparatus of claim 1 wherein the rod-like element is comprised of a polyurethane material.

5. The stabilizer apparatus of claim 1 wherein the bearing of the first engagement member includes a hole that is configured to receive a threaded portion of the first pedicle screw.

6. The stabilizer apparatus of claim 1 wherein the rod-like element includes two recesses formed in mutually opposite lateral surfaces of the rod-like element and accommodate the cord when the cord forms a closed loop around the rod-like element.

7. The stabilizer apparatus of claim 1 wherein the cord is provided, at one end, with a plurality of teeth for fastening within an accommodation mechanism provided at the opposite end of the cord.

8. The stabilizer apparatus of claim 1 wherein the protruding portion of the first engagement member includes a second hole configured to receive a threaded locking member which locks the rod-like element within the protruding portion of the first engagement member.

9. A stabilizer apparatus for a spinal column, comprising:

a first disk-like engagement means housing a bearing means and having at least one protruding portion with a seat for receiving a rod-like element, where the protruding portion includes a through hole having a longitudinal axis extending transverse with a longitudinal axis of the rod-like element, and the bearing means is configured to receive a first pedicle screw and rotates within the first disk-like engagement means; and a second disk-like engagement means housing a bearing means and having at least one protruding portion with a seat for receiving a rod-like element, where the protruding portion includes a through hole having a longitudinal axis extending transverse with a longitudinal axis of the rod-like element, and the bearing means is configured to receive a second pedicle screw and rotate within the second disk-like engagement means, wherein the first disk-like engagement means is connected via the rod-like element to the second disk-like engagement means and a cord extends through the through holes of the protruding portions of the first and second disk-like engagement means with its ends coupled together to form a closed loop around the rod-like element, the protruding portions of the first and second disk-like engagement means facing each other.

10. The stabilizer apparatus of claim 9 wherein at least one of the first disk-like engagement means and the second disk-like engagement means includes a second protruding portion arranged diametrically opposite the first protruding portion and with a seat for receiving another rod-like element.

11. The stabilizer apparatus of claim 10 wherein the bearing means of the first disk-like engagement means includes a hole that is configured to receive a threaded portion of the first pedicle screw.

12. The stabilizer apparatus of claim 11 wherein the rod-like element includes two recesses formed in mutually opposite lateral surfaces of the rod-like element and accommodate the cord when the cord forms a closed loop around the rod-like element.

13. The stabilizer apparatus of claim 12 wherein the cord is provided, at one end, with a plurality of teeth for fastening within an accommodation means provided at the opposite end of the cord.

14. The stabilizer apparatus of claim 9 wherein the rod-like element is comprised of elastic material.

15. The stabilizer apparatus of claim 9 wherein the rod-like element is comprised of a polyurethane material.

* * * * *